(12) United States Patent
Costonis

(10) Patent No.: US 9,714,894 B2
(45) Date of Patent: Jul. 25, 2017

(54) AGGREGATE MIXTURE ANALYSIS DEVICE

(76) Inventor: Joel F. Costonis, Dexter, ME (US)

(*) Notice: Subject to any disclaimer, the term of this patent is extended or adjusted under 35 U.S.C. 154(b) by 0 days.

(21) Appl. No.: 11/456,880

(22) Filed: Jul. 12, 2006

(65) Prior Publication Data

US 2008/0011110 A1    Jan. 17, 2008

(51) Int. Cl.
| | |
|---|---|
| G01N 33/00 | (2006.01) |
| B07B 13/00 | (2006.01) |
| B07B 1/26 | (2006.01) |
| B07B 1/38 | (2006.01) |
| G01N 15/06 | (2006.01) |

(52) U.S. Cl.
CPC ................. G01N 15/0606 (2013.01)

(58) Field of Classification Search
USPC ...... 73/866, 863.12; 209/239, 233, 309, 350
See application file for complete search history.

(56) References Cited

U.S. PATENT DOCUMENTS

| | | | | |
|---|---|---|---|---|
| 2,713,977 | A | * | 7/1955 | Noll .............................. 241/79.2 |
| 5,222,605 | A | * | 6/1993 | Pogue ........................... 209/239 |
| 5,943,234 | A | | 8/1999 | Martinez et al. ................ 700/97 |
| 6,711,957 | B2 | | 3/2004 | Martinez et al. ................ 73/824 |
| 6,817,230 | B2 | | 11/2004 | James et al. ........................ 73/73 |
| 6,826,498 | B2 | | 11/2004 | Birkner et al. .................. 702/84 |
| 2002/0073776 | A1 | | 6/2002 | James et al. ..................... 73/433 |
| 2003/0217604 | A1 | | 11/2003 | Martinez et al. ................ 73/824 |
| 2004/0039467 | A1 | | 2/2004 | Martinez et al. ................ 700/97 |
| 2005/0016291 | A1 | | 1/2005 | Martinez et al. ................ 73/824 |

* cited by examiner

*Primary Examiner* — Hezron E. Williams
*Assistant Examiner* — Tamiko D Bellamy

(57) ABSTRACT

A self-contained portable device for performing multiple tests on samples of hot asphalt mix and providing an analysis of the aggregate mixture of those samples, comprising an external housing which contains the other components, a test chamber into which samples are placed for analysis, a plurality of sieves located within the test chamber for separating and sorting aggregates, a drive shaft for rotating the sieves, guide rails for directing the rotation of the sieves in a multidirectional tilt pattern, a weighing component for weighing the samples, a wash component for directing water or other liquids into the test chamber and onto the samples, a heating component for raising the temperature of the test chamber, a pressure control component to lower the pressure within the test chamber, a controller to operate the various components, and a computer and computer software to process the results of the various tests and to prepare an analysis therefrom.

30 Claims, 8 Drawing Sheets

AGGREGATE MIXTURE ANALYSIS DEVICE

BACKGROUND OF THE INVENTION

1. Technical Field

The invention relates generally to the field of analyzing aggregate mixtures for purposes of determining acceptability of same for use. More specifically, the invention is directed to an improved analysis device suitable for performing multiple analyses on a given test sample of aggregate mixture.

2. Description of Prior Art

Modern roadways, parking lots, airport taxiways and landing strips, sidewalks, and other surfaces designed to accommodate wheeled vehicles are often paved and repaired using a composite material comprised of aggregates and binders. Pavement, concrete, and certified aggregates are comprised of a mixture of aggregates of varying sizes, from fine sand to small rocks, some combined with liquid binder.

Aggregate mixtures may be formulated to have varying properties, including strength, flexibility, water-resistance, cracking resistance, cost-effectiveness, and the like. Required properties for different applications are well known in the art and are subject to extensive industry and governmental regulation and guidelines. These properties are controlled by the proportion of aggregate or aggregate to binder and the physical nature of the aggregate itself. The size, shape, and hardness of the aggregate, along with its moisture content and amount of air entrapped therein, affect the ultimate properties of the resulting aggregate mixture.

Because of the dependency of aggregate mixtures on their correct properties, various formulations have been developed for different applications, and builders will specify the appropriate formulations for their projects. These formulations specify the proportions of various types of coarse to fine aggregates to be included and the ratio of aggregate to binder. However, the aggregate mixtures are not available as "off the shelf" products but rather must be produced and individually blended as per owner specifications from raw materials generally close in time to its use. The quantities of aggregates used is typically measured in tons, while individual pieces may be measured by the millimeter or even less, and thus the input materials can be classified at best only by their presumed gross average characteristics, introducing the potential for error. As a result, the resulting mixture often may not achieve all of the required properties. Testing protocols, therefore, have been devised for determining whether a freshly produced aggregate mixture meets the specified requirements. These protocols involve taking multiple samples of the completed mixture and testing each sample by deconstructing it into its component materials and comparing same to known standards. Different protocols involve weighing the samples and their component materials, measuring aggregate size, measuring moisture content, measuring air voids, and the performance of other tests. Many of these tests are typically performed in laboratories, using multiple large, special purpose devices for the various types of tests.

The known art is replete with devices to test samples of aggregate in order to analyze the properties of the mixture. There are sieving devices to sort aggregates by size, typically coupled with means for weighing the sorted quantities. These sieving devices typically use a vibratory motion to shake the aggregate through the sieves. There are devices which perform ignition testing, in which the binder is burned off. There are devices for measuring the specific gravity of samples, typically using water submersion techniques. There are devices for measuring theoretical maximum densities. Many of these tests are performed under pressure or in heated conditions.

Most of the devices known in the art for performing tests on samples of aggregate mixtures are very large and cannot be easily transported to a job site, and thus time is lost in transporting samples to the devices. Time is also lost in transferring samples from device to device to perform the various tests. Many of the known devices also do not perform their specific tests efficiently, leading to more lost time, as well as being prone to damaging the sample components, which can yield inaccurate results.

There is thus a long-felt need in the industry for a device which addresses the deficiencies in the known art, specifically a device which combines many testing functions in a single small, portable, self-contained unit which performs its tests quickly, efficiently, and accurately.

SUMMARY OF THE INVENTION

The present invention is a self-contained device for performing multiple tests on samples of aggregates and providing an analysis of the results of those tests. Because these tests are performed in a single device, the testing process is more efficient than with known devices, as the sample need not be handled as much and the time between tests is minimized. The present invention employs novel means for performing known tests which speeds the testing process and which minimizes damage to the samples, thus leading to more accurate results. The device is also small enough to be easily transportable to the job site, further minimizing time lost in transporting samples to an off-site laboratory.

The preferred embodiment of the present invention comprises an external housing which contains the other components; a test chamber into which samples are placed for analysis; a plurality of sieves located within the test chamber for separating and sorting aggregates; a drive shaft for rotating the sieves; guide rails for directing the rotation of the sieves in a multidirectional tilt pattern; a weighing component for weighing the samples; a wash component for directing water or other liquids into the test chamber and onto the samples; a heating component for raising the temperature of the test chamber to assist in drying the samples and to effect ignition testing; a pressure control component to create a lower pressure within the test chamber; a controller to operate the various components, and a computer and computer software to process the results of the various tests and to prepare an analysis therefrom.

Samples are separated and sorted by operation of the plurality of sieves, with the sieves ordered vertically within the test chamber onto the drive shaft. The sieves are arranged by order of mesh size, with the sieves having larger mesh openings positioned above sieves having smaller mesh openings. Samples are sifted through the sieves by rotating the sieves with the drive shaft. The guide rails tilt the sieves as they rotate, causing the samples to roll along the mesh of the sieves. This novel spin-and-tilt operation improves upon the typical high speed vibratory agitation of known sieving devices, in that aggregate is effectively sieved without the risk of fracturing inherent in vibratory agitation. Minimizing aggregate fractures improves the accuracy of the testing by reducing false readings biased towards finer aggregates.

Samples are weighed within their respective sieves by operation of a weighing assembly integrated with the drive shaft. The drive shaft is raised incrementally, lifting the lowermost sieve, and the entire assembly plus the sieve plus the sample contained therein is weighed. The drive shaft is again raised incrementally, lifting the lowermost sieve until it contacts the next higher sieve, then raising both, with the entire assembly weighed again, together with the two sieves plus the samples contained therein. This process is repeated for the remaining sieves, such that each incremental lift results in obtaining a new partial gross weight of the entire assembly plus the lifted sieves plus the samples contained therein. The tare weights of the assembly and sieves may then be subtracted to obtain the weights of the individual samples located within each sieve.

Samples are processed with the test chamber in various ways. The wash component is used to wash the samples, assisting in separating fine particulates from the remainder of the aggregate. In one embodiment a single inlet is used; in another embodiment multiple inlets are used, directed to the individual sieves and independently controlled. The heating component is used to dry the samples after washing. The heating component may also be used to conduct ignition testing. These processes may be conducted under reduced pressure. Being subjected to reduced pressure increases the efficiency of the processes; for example, drying is accomplished faster since water boils at lower temperatures under reduced pressure. It also allows for more efficient testing of theoretical maximum density, by which the air voids in a sample are measured, in that the air in the voids is more easily released when the sample is subjected to a pressure lower than ambient pressure. The samples may be weighed prior to, during, and after these processes.

Weight data obtained from the various testing of the samples are provided to the computer, which interfaces with the weighing assembly. The computer also has a user interface for entering and displaying data. The computer software is suitably adapted to run on the computer and to process data provided by the user and obtained from the testing of the samples, to provide a meaningful analysis of the properties of the aggregate mixture. In one embodiment the various testing components are controlled by the computer and the computer software, as are inputs from various sensors incorporated within the test chamber. The sample analysis is conducted on site and allows for the immediate acceptance or rejection of the aggregate mixture based on the analysis.

It is an objective of the present invention to provide a useful, improved aggregate mixture analysis device which combines many testing functions in a single unit.

It is a further objective of the present invention to provide a useful, improved aggregate mixture analysis device which is portable and transportable to the job site.

It is a further objective of the present invention to provide a useful, improved aggregate mixture analysis device which performs its tests quickly and efficiently, with a minimal amount of handling of the test samples.

It is a further objective of the present invention to provide a useful, improved aggregate mixture analysis device which performs its tests accurately.

It is a further objective of the present invention to provide a useful, improved aggregate mixture analysis device which performs its tests with a minimum of damage to testing samples.

It is a further objective of the present invention to provide a useful, improved low cost aggregate mixture analysis device.

Other objectives of the present invention will be readily apparent from the description that follows.

DETAILED DESCRIPTION OF THE INVENTION

Figure 1:
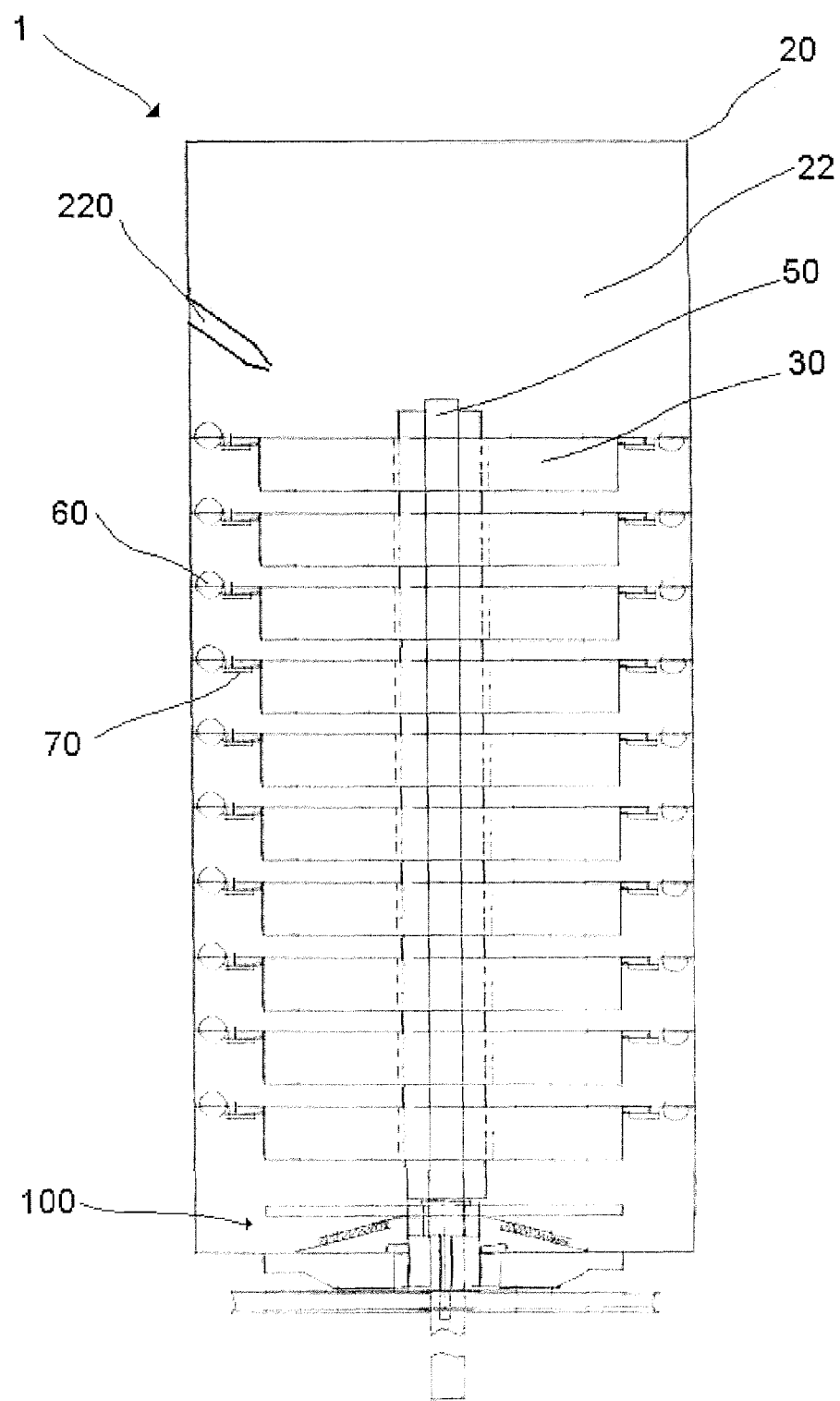
FIG. 1 is a schematic plan view of the device of the present invention depicting its primary components, including the test chamber, sieves, drive shaft, and lift assembly.

The present invention is directed to an improved self-contained device 1 for performing multiple tests and analyses on samples of aggregate mixture.

The improved aggregate mixture analysis device 1 of the present invention comprises a housing 10, a test chamber 20, a plurality of sieves 30 for sifting the aggregate mixture into quantities of similarly sized pieces, a drive shaft 50 for rotating and lifting the sieves 30, a rotary drive 80 for rotating the drive shaft 50, a lift assembly 100 for lifting and lowering the drive shaft 50, a weighing assembly 90 comprising a load cell 92 for weighing the drive shaft 50 and any sieves 30 engaged upon the drive shaft 50 and any aggregate mixture contained within the sieves 30, a plurality of guide rails 60 for orienting the rotational direction of the sieves 30, a wash component for washing the aggregate mixture, a heating component, a pressure control component for lowering the pressure within the interior 22 of the test chamber 20 in respect to ambient pressure, a control component for controlling the operation of the rotary drive 80, the lift assembly 100, the weighing assembly 90, the wash component, the heating component, and the pressure control component, and a computer and computer software for providing a meaningful analysis of the aggregate mixture.

Figure 2:
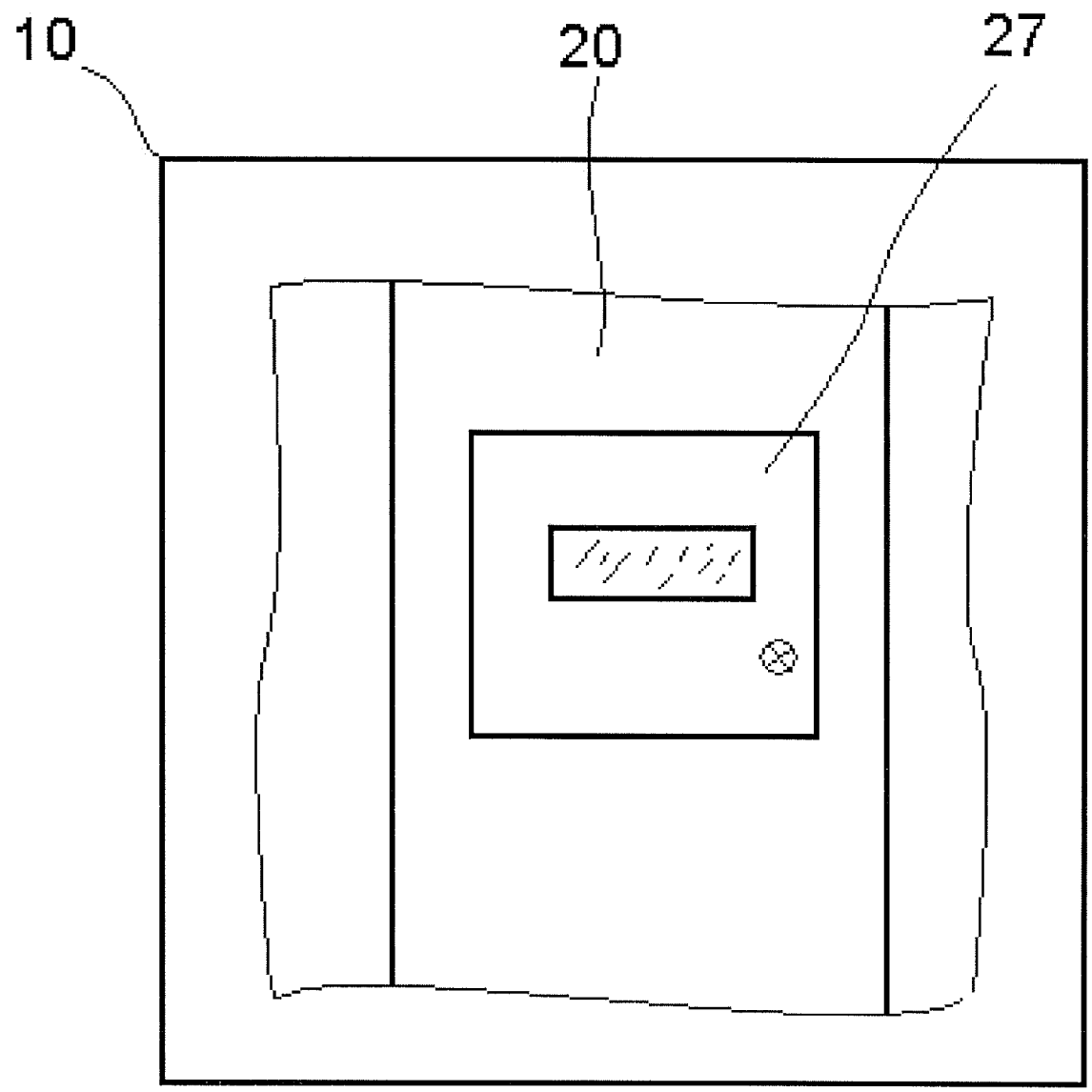
FIG. 2 is a schematic plan view of the device of the present invention depicting the relationship of the test chamber to the housing.

The housing 10 may be of any suitable size and shape, provided it encloses an interior within which the other components of the device 1 may be located. See FIG. 2. In the preferred embodiment the housing 10 is constructed of metal, and contains one or more access means, such as doors or hatches, to access the interior. In the most preferred embodiment the housing 10 is small enough to make the device 1 portable, for example by pickup truck, to remote locations.

The test chamber 20 is designed to contain the aggregate mixture to be analyzed. The test chamber 20 is substantially cylindrical and has a hollow interior space 22 defined by an interior wall 24, and the test chamber 20 is oriented substantially vertically within the housing 10. See FIG. 1. The test chamber 20 may be constructed of any suitable material or materials; in the preferred embodiment it is constructed of metal. The interior diameter of the test chamber 20 is suitably adapted to accommodate the plurality of sieves 30 in a substantially horizontal orientation. It also contains the drive shaft 50 and, along its interior wall 24, the guide rails 60.

The test chamber 20 has an access mechanism having an opened state and a closed state, whereby access into the interior space 22 of the test chamber 20 is afforded through the access mechanism when the access mechanism is in the opened state, and access into the interior space 22 of the test chamber 20 is prevented when the access mechanism is in the closed state. The aggregate mixture to be analyzed by the device 1 is placed into the test chamber 20 by use of the access mechanism. In the preferred embodiment the access mechanism of the test chamber 20 comprises a hinged cover 27. See FIG. 2. The hinged cover 27 may contain a transparent window for viewing the interior space 22 of the test chamber 20 when the hinged cover 27 is in the closed position. Other configurations of the access mechanism, such as a sliding door, a removable hatch, and the like, are also contemplated. The test chamber 20 is further suitably adapted to maintain a pressure lower than the ambient pressure when the access mechanism is in the closed state. This may be achieved by employing gaskets or other sealing devices within the test chamber 20 to render the test chamber 20 substantially air-tight when the access mechanism is in the closed state.

Figure 5:
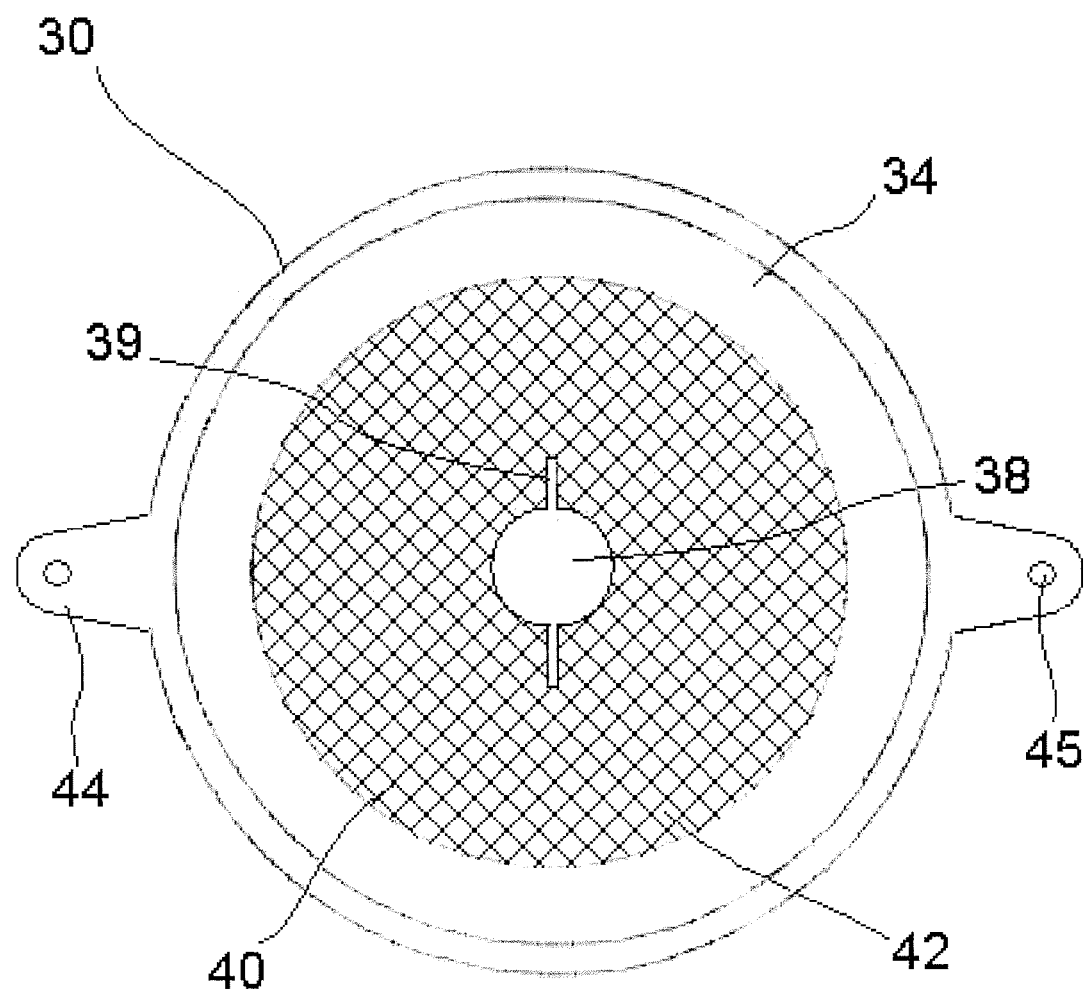
FIG. 5 is a top view of a sieve, along with a top view of the drive shaft having opposing vertical flanges.
Figure 5:
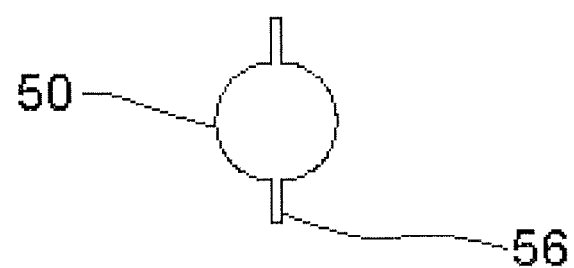

The sieves 30 are each suitably adapted to retain a quantity of aggregate mixture, with each sieve 30 having an open top 32, a substantially vertical circumferential sidewall 34, and a substantially planar, circular bottom 36 comprising a mesh 40. See FIG. 5. The substantially vertical circumferential sidewall 34 may be angled slightly upward and outward. The mesh 40 of each sieve 30 has a plurality of apertures 42 of substantially uniform size. The size of the apertures 42 of the mesh 40 of each sieve 30 is different than the sizes of the apertures 42 of the mesh 40 of each other sieve 30. As such, the sieves 30 may be ordered vertically within the test chamber 20, with the sieve 30 with the largest mesh apertures 42 placed highest within the test chamber 20 and successively lower sieves 30 having successively smaller mesh apertures 42, so that the sieve 30 with the smallest mesh apertures 42 is placed lowest within the test chamber 20. See FIG. 1. With the sieves 30 so arranged, a sample of aggregate mixture may be placed within the topmost sieve 30 and caused to be sifted through that sieve 30 and the lower sieves 30. Only the portion of the aggregate mixture placed within the topmost sieve 30 having the largest components will be retained in that sieve 30; the remaining portions of the aggregate mixture will fall through the mesh 40 into the sieve 30 directly below. Likewise, the portion of the aggregate mixture sifted into the sieve 30 directly below the topmost sieve 30 having the largest components will be retained in that sieve 30 and the remaining portions of the aggregate mixture will fall through the mesh 40 into the next sieve 30 directly below. This sifting continues until the smallest components of the aggregate mixture fall through the lowermost sieve 30, with each sieve 30 containing substantially uniformly sized components of the original sample of the aggregate mixture.

Figure 4:
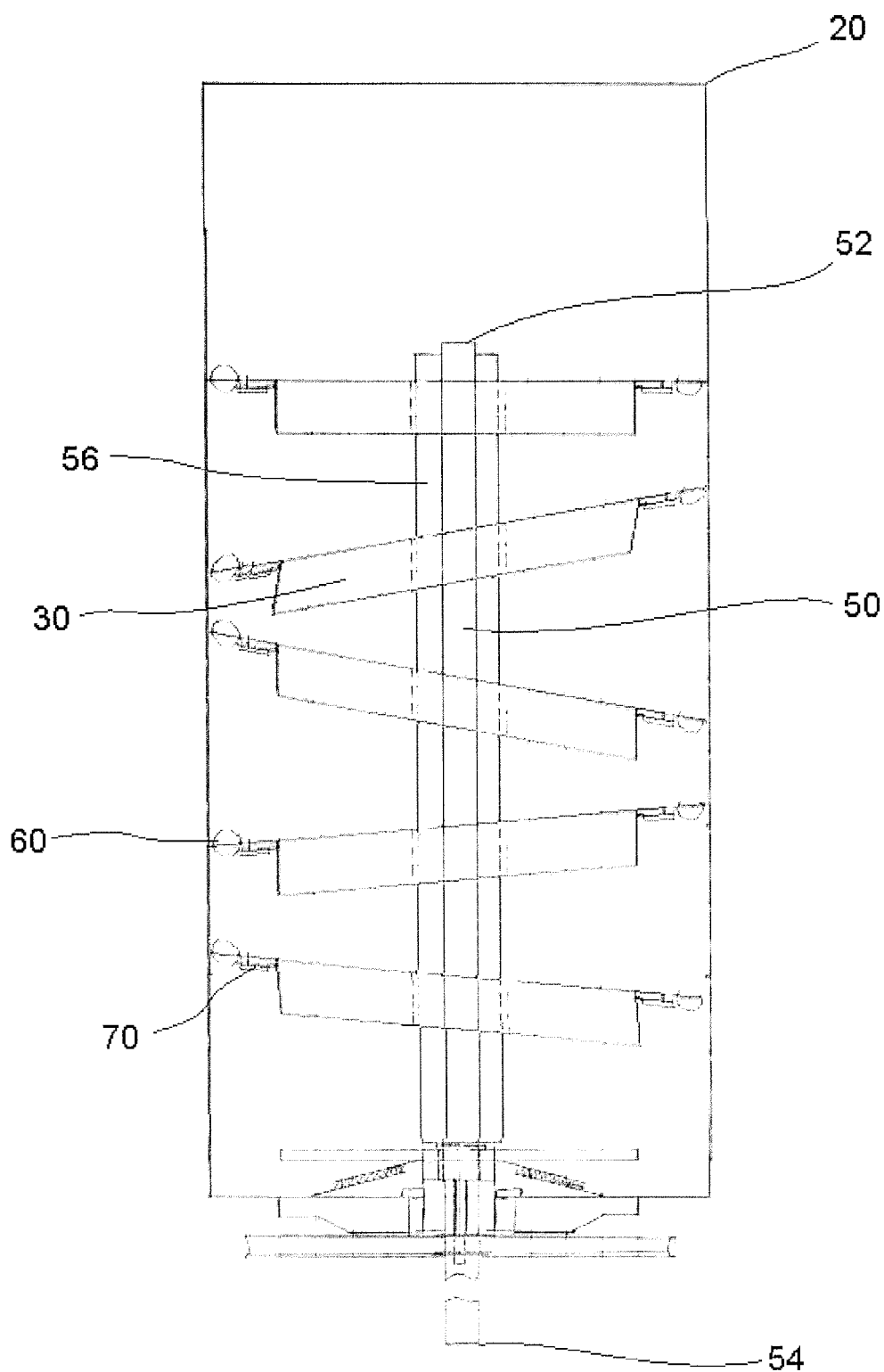
FIG. 4 is a schematic plan view of the device of the present invention depicting relative orientations of the sieves during the spin-and-tilt sifting operation.

Each sieve 30 comprises a central aperture 38 formed within its circular bottom 36, suitably adapted to accommodate the drive shaft 50. See FIG. 5. The drive shaft 50 is substantially cylindrical and elongate, and has an upper end 52 and a lower end 54. See FIG. 4. The drive shaft 50 is oriented substantially vertically and located within the interior space 22 of the test chamber 20, substantially centered therein. The drive shaft 50 is suitably adapted to rotate about its longitudinal axis by action of the rotary drive 80. The sieves 30 are placed onto the drive shaft 50 through the central apertures 38 of the sieves 30. The drive shaft 50 is further adapted to engage the sieves 30 through their respective central apertures 38 such that when the drive shaft 50 rotates it simultaneously rotates each sieve 30 engaged thereupon. The drive shaft 50 is further adapted to move in a vertical direction, both upward and downward within the test chamber 20, by action of the lift assembly 100. When moving in an upward direction the drive shaft 50 sequentially lifts each sieve 30 engaged thereupon. When moving in a downward direction the drive shaft 50 sequentially lowers each sieve 30 engaged thereupon.

In one embodiment the drive shaft 50 further comprises a pair of opposing vertical flanges 56, each said flange 56 running from the upper end 52 to the lower end 54 of the drive shaft 50, and each sieve 30 further comprises a pair of opposing slots 39 emanating from the central aperture 38, said slots 39 substantially aligned with the pair of opposing flanges 56 of the drive shaft 50, which are suitably adapted to fit within one of the opposing slots 39 of each sieve 30. See FIG. 5. In this embodiment, a rotation of the drive shaft 50 causes the pair of vertical flanges 56 to engage the sides of the slots 39 of the central apertures 38 of the sieves 30, thereby rotating the sieves 30 simultaneously with the drive shaft 50. However, when the drive shaft 50 is lifted or lowered, the flanges 56 of the drive shaft 50 slide within the slots 39 without causing vertical movement of the sieves 30.

Figure 7:
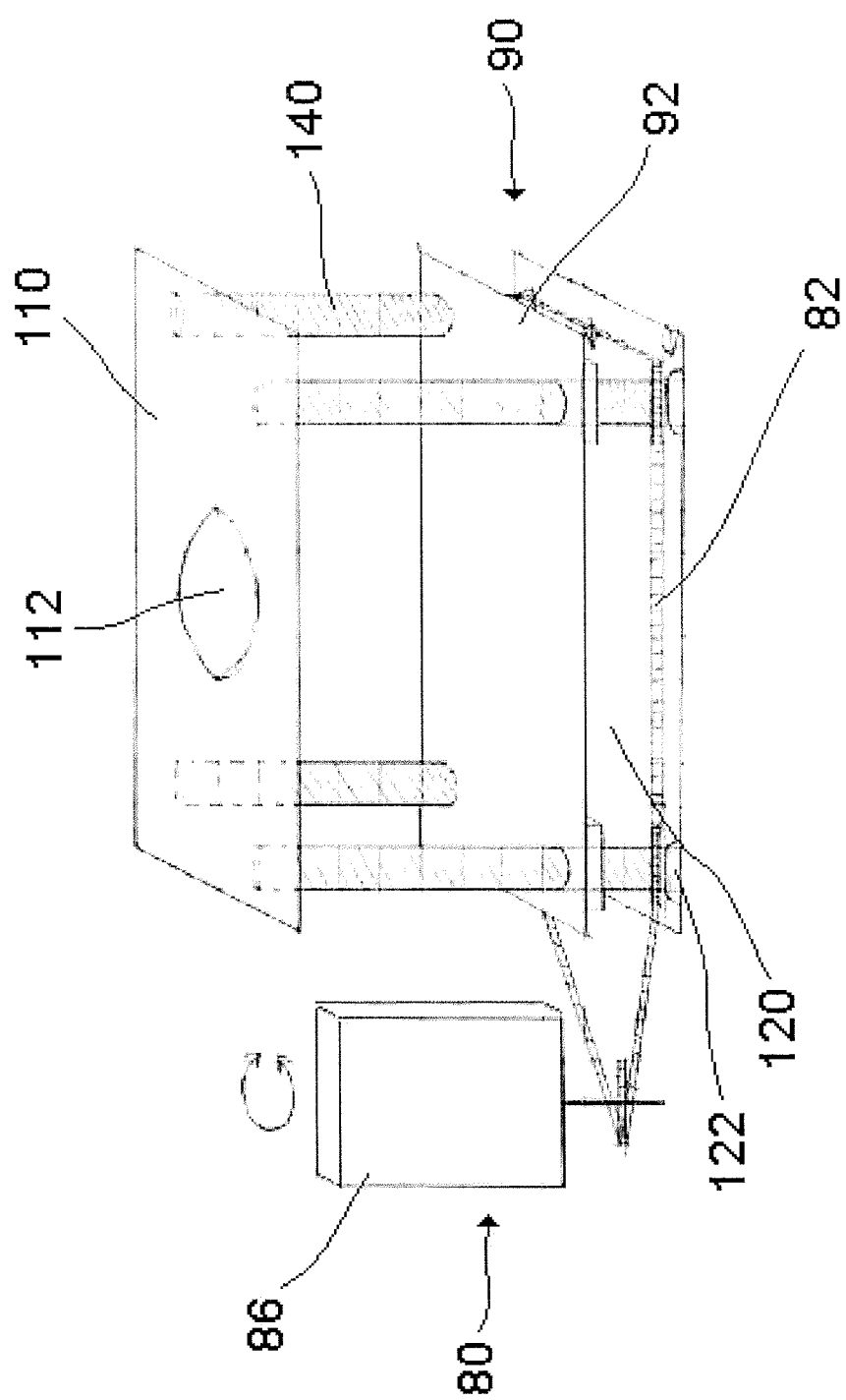
FIG. 7 is a perspective view of the lift assembly/weighing assembly/rotary drive.

The rotary drive 80 is located within the housing 10 below the test chamber 20, and is suitably adapted to rotate the drive shaft 50. In the preferred embodiment the rotary drive 80 may rotate the drive shaft 50 in both a clockwise and a counterclockwise direction. In one embodiment the rotary drive 80 comprises an electric motor 86 and a pulley system 82. See FIG. 7. The electric motor 86 is suitably adapted to operate the pulley system 82, and the pulley system 82 is suitably adapted to engage the drive shaft 50 to cause the drive shaft 50 to rotate. In the preferred embodiment the rotary drive 80 further comprises a coupler attached to the pulley system 82, whereby the coupler is suitably adapted to engage the pair of opposing vertical flanges 56 located on the sides of the drive shaft 50, as described above. The coupler has a central aperture and a pair of opposing slots suitably adapted to align with and loosely accommodate the flanges 56 of the drive shaft 50. The lower end 54 of the drive shaft 50 is placed into the central aperture of the coupler and the flanges 56 of the drive shaft 50 are placed within the slots of the coupler. When operation of the electric motor 86 moves the pulley system 82, the pulley system 82 causes the coupler to rotate, with the slots of the coupler engaging the flanges 56 of the drive shaft 50, thereby rotating the drive shaft 50 simultaneously with the coupler. However, when the drive shaft 50 is lifted or lowered, the flanges 56 of the drive shaft 50 slide within the slots of the coupler without causing vertical movement of the coupler. Other embodiments contemplate different rotary drive 80 configurations that may be known in the art. For example, a shaft and gear configuration could be used to rotate the drive shaft 50.

The lift assembly 100 is located within the housing 10 below the test chamber 20, and is suitably adapted to lift and lower the drive shaft 50. In one embodiment the lift assembly 100 comprises a lift plate 110, a base plate 120, a plurality of threaded shafts 140, a pulley system, and a reversing electric motor, as well as the load cell 92 of the weighing assembly 90. See FIG. 7. The lift plate 110 is substantially planar and oriented substantially horizontally, and has an aperture 112 suitably adapted to allow the lower end 54 of the drive shaft 50 to pass through it. The base plate 120 is substantially planar and has a top surface and a perimeter. The base plate 120 is oriented substantially horizontally and below the lift plate 110. It has a plurality of sockets 122 disposed on its top surface about its perimeter. Each of the plurality of threaded shafts 140 has an upper end and a lower end, with each lower end of the threaded shafts 140 suitably adapted to be placed within a socket 122 of the base plate 120 and suitably adapted to rotate within that socket 122. Each of the threaded shafts 140 is oriented substantially vertically. The load cell 92 of the weighing assembly 90 is substantially planar and has an upper surface and a lower surface and a perimeter. The load cell 92 is oriented substantially horizontally and interposed between the base plate 120 and the lift plate 110 of the lift assembly 100. It is suitably adapted to support the lower end 54 of the drive shaft 50. The load cell 92 has threaded apertures disposed on its lower surface about its perimeter, with the threaded apertures substantially aligned with the upper ends of the threaded shafts 140 of the lift assembly 100 such that the threaded shafts 140 pass into and through the threaded apertures of the load cell 92. The load cell 92 further comprises a support structure on its upper surface, with the support structure suitably adapted to support the lift plate 110 of the lift assembly 100.

The pulley system of this embodiment of the invention is suitably adapted to engage the threaded shafts 140 of the lift assembly 100 and to rotate the threaded shafts 140 in either of two opposite rotational directions, simultaneously rotating all of the threaded shafts 140 in the same rotational direction and at the same rotational speed. The reversing electric motor is suitably adapted to operate the pulley system in the two opposite rotational directions. In one embodiment the same electric motor 86 may be used to operate both the lift assembly 100 and the rotary drive 80. In this configuration, the rotation of the threaded shafts 140 of the lift assembly 100 in one direction causes the load cell 92 of the weighing assembly 90 to move upwards along the threads of the threaded shafts 140, lifting the drive shaft 50. Once the support structure of the load cell 92 contacts the lift plate 110 of the lift assembly 100 the load cell 92 lifts it as well. This causes the lift plate 110 to come in contact with the lowermost sieve 30 and lift that sieve 30. As the lift assembly 100 continues to move in an upward direction it will continue to lift the lowermost sieve 30 until that sieve 30 comes in contact with the sieve 30 next above and lifts that sieve 30 as well. The lift plate 110 may continue to move upward until each sieve 30 is contacted by and lifted by the sieve 30 immediately below it. The weighing assembly 90, integrated with the lift assembly 100 by means of its load cell 92, is suitably adapted to register the weight of the items supported on the load cell 92 at any given time. This includes only the drive shaft 50, then the drive shaft 50 plus the lowermost sieve 30, together with any aggregate mixture contained within that sieve 30, then the drive shaft 50 plus the two lowermost sieves 30, together with any aggregate mixture contained within those sieves 30, and so on until all the sieves 30 together with any aggregate mixture contained within the sieves 30 have been weighed. Each individual weight registered by the weighing assembly 90 is communicated to the computer and computer software, which in turn calculates the weight of the aggregate mixture contained within each sieve 30. The rotation of the threaded shafts 140 of the lift assembly 100 in the opposite direction causes the load cell 92 of the weighing assembly 90 to move downward along the threads of the threaded shafts 140, lowering the lift plate 110 and the drive shaft 50, such that each sieve 30 resting upon the sieve 30 immediately below it becomes separated from that sieve 30 in sequence, from the topmost sieve 30 to the lowermost sieve 30, with the lift plate 110 finally separating from the lowermost sieve 30.

The sieves 30 are not only rotated by the drive shaft 50 but are tilted within continually varying multidirectional planes. That is, the plane of each sieve 30 tilts away from the horizontal as the sieve 30 is rotated, tilting as much as +/−30° from the horizontal. See FIG. 4. This tilting action of the sieves 30 causes the aggregate mixture contained therein to roll along the mesh 40 of the sieves 30, such that smaller sized portions may pass through the mesh 40 and fall out of the sieve 30. This novel spin-and-tilt operation improves upon the typical high speed vibratory agitation of known sieving devices, in that the gentle rotation and tilting of the aggregate mixture minimizes the risk of fracturing the sample inherent in high speed vibratory agitation. Minimizing aggregate fractures improves the accuracy of the testing by reducing false readings biased towards finer aggregates.

Figure 3:
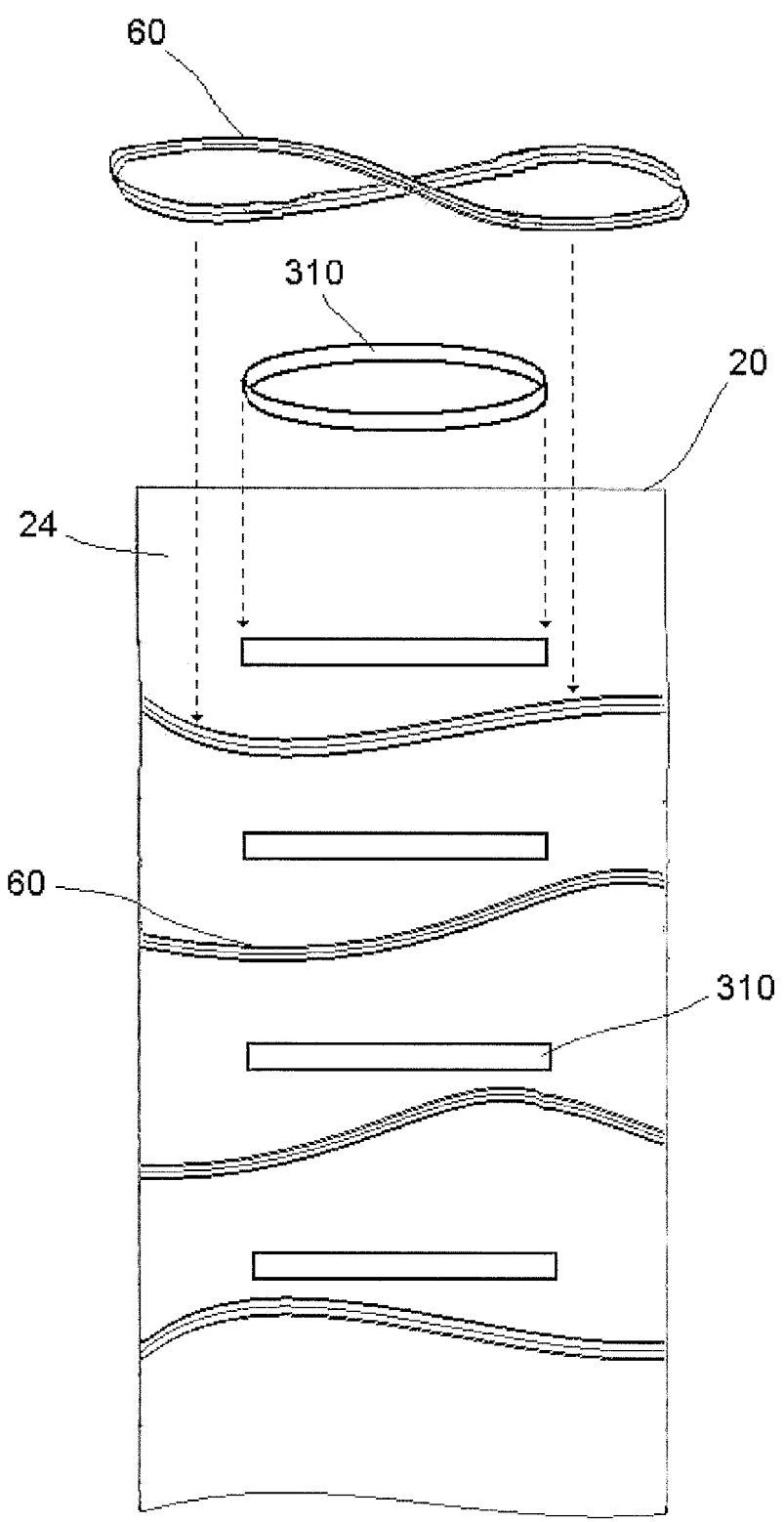
FIG. 3 is a schematic plan view of the device of the present invention depicting the interior wall of the test chamber and the location thereon of the guide rails and the heating elements, with an exemplar of one guide rail and one heating element shown in perspective.

The spin-and-tilt operation is accomplished by the test chamber 20 incorporating a plurality of guide rails 60 along its interior wall 24. See FIG. 3. The number of guide rails 60 corresponds in number to the maximum number of sieves 30, with each guide rail 60 associated with a sieve 30. The guide rails 60 are located within the interior space 22 of the test chamber 20 circumferentially along the interior wall 24 of the test chamber 20 and proximate to the location of a sieve 30 placed upon the drive shaft 50. Each guide rail 60 is continuous and has a varying degree of slope from the horizontal, with the slope changing uniformly about the circumference of the guide rail 60. Each of the plurality of guide rails 60 has substantially the same shape as each other guide rail 60, with each of the guide rails 60 offset in relation to an adjacent guide rail 60 by a rotation of between 10° and 30°. All of the guide rails 60 have the same degree of offset from adjacent guide rails 60. This causes falling aggregate mixture to contact a next lower sieve 30 at an angle different from the angle at which it passed through the mesh 40 of the prior sieve 30. This redirection of falling aggregate mixture improves its separation and increases the efficiency of the sifting operation.

Figure 6:
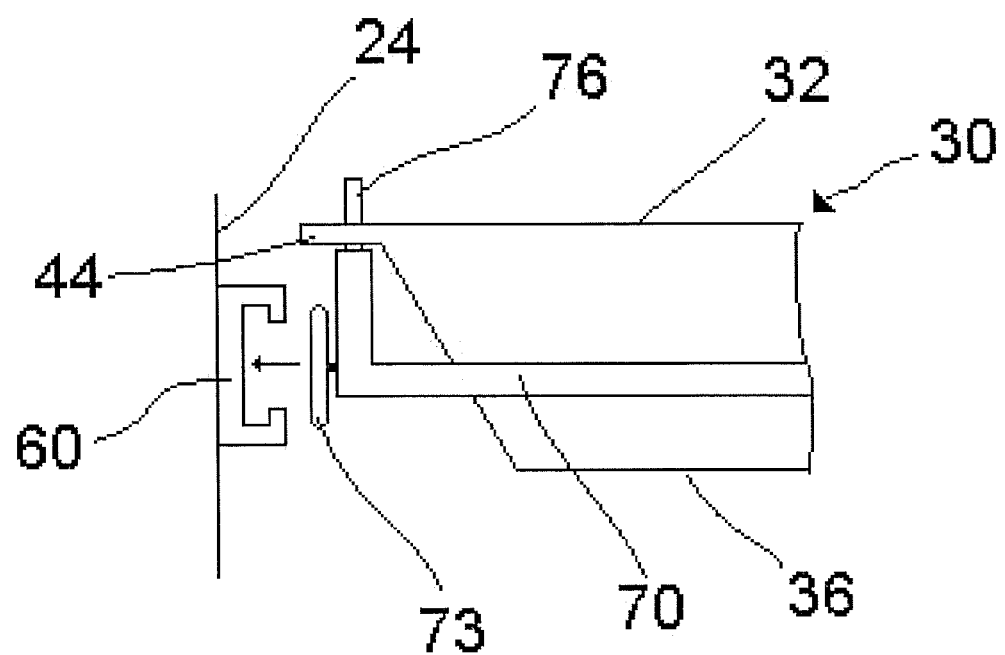
FIG. 6 is a side view of a guide rail, ride ring, and sieve, along with a top view of the sieve showing the relationship of the guide rail, ride ring, and sieve.
Figure 6:
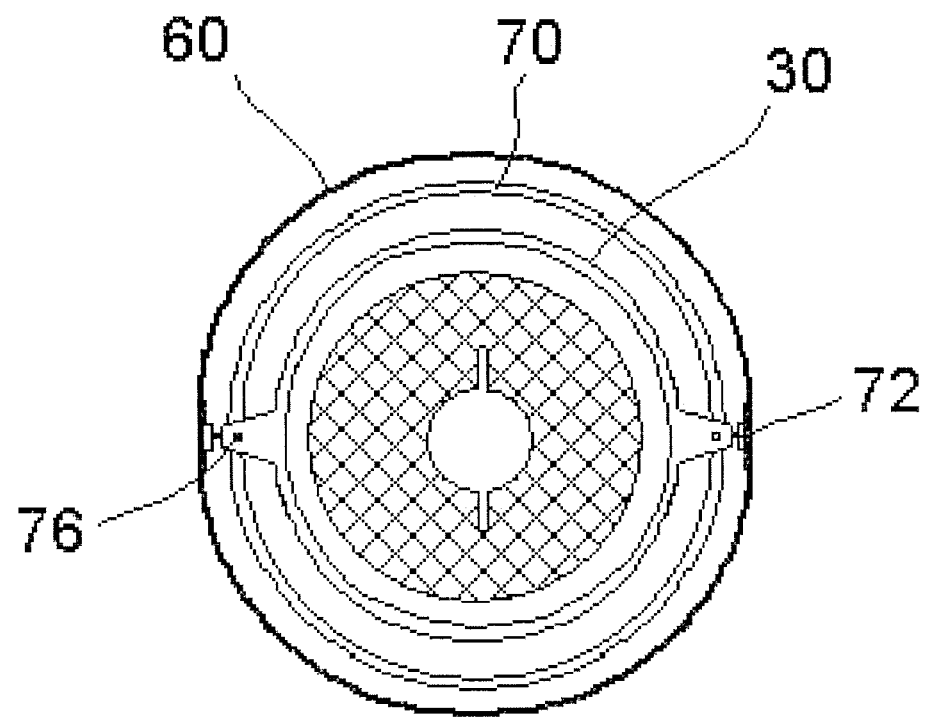

The guide rails 60 are suitably adapted to engage with corresponding sieves 30 such that when the sieves 30 are rotated the varying slope of the guide rail 60 causes the corresponding engaged sieve 30 to tilt in a multiplicity of varying directions between positive 30° to negative 30° from the horizontal. In the preferred embodiment each sieve 30 engages with a corresponding guide rail 60 by a ride ring 70. See FIG. 6. Each ride ring 70 is substantially circular and has a plurality of engagement elements 72, the engagement elements 72 suitably adapted to engage with the associated guide rail 60 such that the ride ring 70 can rotate along the associated guide rail 60. Each ride ring 70 if further suitably adapted to contain and engage with a sieve 30, such that when the sieve 30 is rotated by the drive shaft 50 the engaged ride ring 70 rotates with the sieve 30 along the guide rail 60. The varying slope of the guide rail 60 causes the ride ring 70 to tilt in a multiplicity of varying directions, which in turn tilts the engaged sieve 30. In the most preferred embodiment the engagement elements 72 of each ride ring 70 are a plurality of wheels 73 suitably adapted to ride within the associated guide rail 60. This wheel-in-track arrangement is well-known in the art. Other arrangements are also contemplated, such as sliders adapted to run along a groove formed into the guide rail 60. In another embodiment each sieve 30 comprises a plurality of horizontal engagement flanges 44, with each engagement flange 44 having an aperture 45. Each ride ring 70 comprises a plurality of upwardly disposed vertical engagement pins 76, with each engagement pin 76 corresponding to an engagement flange 44 of a corresponding sieve 30. The engagement pins 76 are suitably adapted to pass through the apertures 45 of the corresponding engagement flanges 44 from below, so that the sieve 30 becomes engaged with the corresponding ride ring 70. Each sieve 30 and each corresponding ride ring 70 may then rotate together when the engagement flanges 44 of the sieves 30 are engaged with the engagement pins 76 of the ride rings 70. In this configuration the engagement flanges 44 of the sieve 30 are suitably adapted to disengage from the engagement pins 76 of the corresponding ride ring 70 when the sieve 30 is lifted by the drive shaft 50 in an upward direction, thereby allowing easy separation of the sieve 30 from the corresponding ride ring 70.

Figure 8:
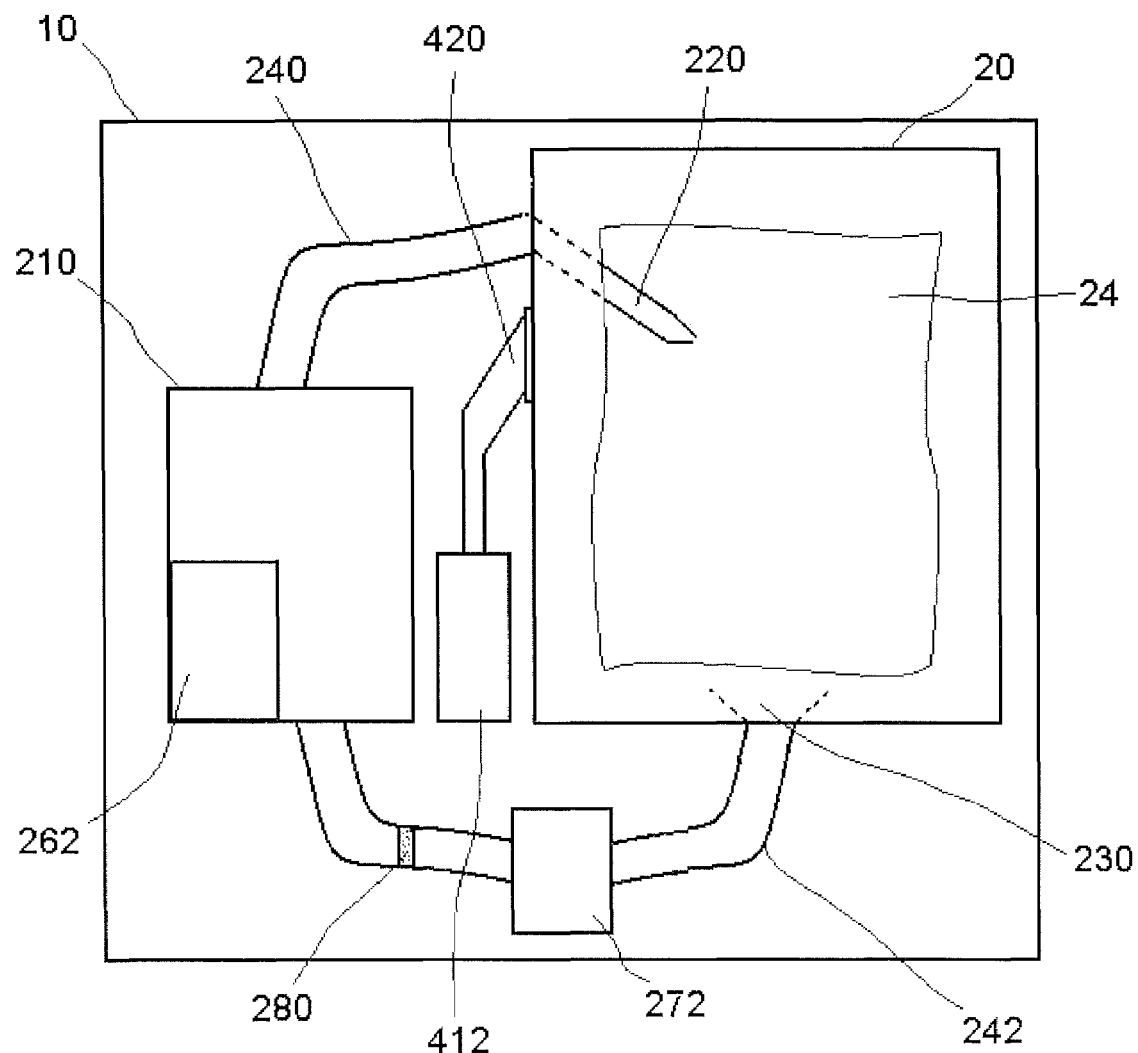
FIG. 8 is schematic plan view of the device of the present invention depicting one embodiment of the wash component/pressure control component.

The wash component, employed to cause water or other liquids to wash over the aggregate mixture within the test chamber 20, is located within the housing 10. In one embodiment it comprises a reservoir 210, an inlet 220, an outlet 230, a conduit 240, and means for moving water or other liquids from the reservoir 210 through the conduit 240 and inlet 220. See FIG. 8. The reservoir 210 is suitably adapted to contain a quantity of water or other liquids. The inlet 220 is integrated with the test chamber 20 and is suitably adapted to introduce water or other liquids into the test chamber 20 and onto at least one of the sieves 30 located therein. The outlet 230 is integrated with the test chamber 20 and is suitably adapted to remove water or other liquids from the test chamber 20. The conduit 240 connects the reservoir 210 to the inlet 220. The means for moving water or other liquids from the reservoir 210 through the conduit 240 and inlet 220 may be a delivery pump 262. In the preferred embodiment the wash component comprises a plurality of inlets 220, with each inlet 220 integrated with the test chamber 20 and suitably adapted to introduce water or other liquids into the test chamber 20 and onto at least one of the plurality of sieves 30 located therein. Associated with the plurality of inlets 220 is a plurality of conduits 240 connecting the reservoir 210 to each inlet 220. In one configuration there is an inlet 220 associated with each sieve 30. In another configuration the quantity of water or other liquids allowed to pass through each of the plurality of inlets 220 is independently controlled. This may be accomplished by use of a valved manifold.

In another embodiment the wash component further comprises a waste pump 272 for moving water or other liquids from the test chamber 20 through the outlet 230. In this embodiment the wash component may further comprise an outflow conduit 242 connecting the outlet 230 to the reservoir 210, with one of more filters 280 interposed within the outflow conduit 242 between the outlet 230 and the reservoir 210. In yet another embodiment the wash component further comprises a sump tank, suitably adapted to contain a quantity of water or other liquids. In this embodiment the outflow conduit 242 connects the outlet 230 to the sump tank.

The heating component is located within the interior space 22 of the test chamber 20 and is suitably adapted to increase the temperature within the interior space 22 of the test chamber 20. See FIG. 3. Increasing the temperature within the interior space 22 of the test chamber 20 decreases the drying time of washed aggregate mixture. It also decreases the time needed to remove naturally occurring moisture from the aggregate mixture. In one embodiment the heating component comprises a plurality of heating elements 310 corresponding in number to the maximum number of sieves 30. Each of the heating elements 310 is substantially circular and located circumferentially along the interior wall 24 of the test chamber 20 proximate to the location of a sieve 30. This allows more efficient application of heat to the aggregate mixture contained within the sieves 30. The heating elements 310 may be electric.

The pressure control component is located within the housing 10 and is in connection with the test chamber 20. See FIG. 8. The pressure control component comprises a pressure lowering device and an interface 420 between the pressure lowering device and the interior space 22 of the test chamber 20. The pressure control component is suitably adapted to lower the pressure within the interior space 22 of the test chamber 20 to less than ambient pressure when the access mechanism of the test chamber 20 is in the closed state. With a lower internal pressure in the test chamber 20 removal of moisture from the aggregate mixture therein occurs more rapidly because moisture will be converted to a gas at a lower temperature. In one embodiment the pressure lowering device is a vacuum pump 412 suitably adapted to introduce a partial vacuum into the interior space 22 of the test chamber 20.

The control component is suitably adapted to control the operation of the rotary drive 80, the lift assembly 100, the weighing assembly 90, the wash component, the heating component, and the pressure control component. This may involve turning on and turning off various components, setting the temperature or pressure levels, determining the amount of fluid to flow through which inlets 220, and the like. In the preferred embodiment the control component is integrated with the computer and the computer software. The control component may interface with the computer by a wired connection. The control component may interface with the computer by a wireless connection. In such configurations, the control component is accessed from the computer. In other embodiments the control component may be mechanical, electrical, hydraulic, or any combination of the foregoing. Any apparatus known in the art which can achieve the control function of the control component is contemplated by the invention.

The computer of the present invention has a user interface for entering and displaying data and a means for interfacing with the weighing assembly 90 such that weights registered by the weighing assembly 90 are received by the computer. The interface may be hard wired or wireless. In one embodiment the means for interfacing the computer with the weighing assembly 90 comprises a removable storage device suitably adapted to interface with both the computer and with the weighing assembly 90, one at a time. For example, a removable thumb drive may be used to interface with the weighing assembly 90 to retrieve data gathered during a weighing operation. The thumb drive may then be removed from the weighing assembly 90 and inserted into the computer, allowing the computer software to access the data. A writable CD, a floppy disk, or any other like media may be used to achieve this result. This allows the potentially more fragile computer to be located distant from the device 1, for example in a nearby construction trailer, to minimize exposure to dust and the elements. The computer software is suitably adapted to run on the computer and is designed to process data received by the computer to provide a meaningful analysis of the aggregate mixture. The computer software may output results in the form of text, graphs, charts, or any other meaningful output.

Arranged within the test chamber 20 are one or more sensors. These sensors are suitably adapted to determine one or more of the following conditions: the opened or closed state of the access mechanism; the proper positioning of the sieves 30; the proper positioning of the drive shaft 50; the interior temperature of the test chamber 20; the interior atmospheric pressure of the test chamber 20; and the level of water or other liquids in the test chamber 20. In the preferred embodiment one or more of the sensors are integrated with the computer and the computer software. This allows the system to monitor itself and give warnings or prevent operation of certain components when the conditions are not appropriate to continue.

Analysis of samples of aggregate mixture is performed by placing samples in the topmost sieve 30 within the test chamber 20, and then performing a combination of one or more of the following steps: sifting the aggregate mixture, washing and/or drying the aggregate mixture, or heating the aggregate mixture while subjecting the aggregate mixture to a low pressure. One or more weighing operations are performed on the aggregate mixture in conjunction with the foregoing steps. All such steps are controlled by the control component, with results from each of the weighing operations provided to the computer to be analyzed by the computer software.

Modifications and variations can be made to the disclosed embodiments of the invention without departing from the subject or spirit of the invention.

I claim:

1. A device for analyzing aggregate mixtures, comprising
   a housing;
   a test chamber, said test chamber being substantially cylindrical and having a hollow interior space defined by an interior wall, said test chamber having an access mechanism having an opened state and a closed state, said access mechanism suitably adapted to permit access into the interior space when in the opened state and to prevent access to the interior space when in the closed state, said test chamber being oriented substantially vertically within the housing, and said test chamber being suitably adapted to maintain a pressure lower than ambient pressure when the access mechanism is in the closed state;
   a plurality of sieves, each said sieve being suitably adapted to retain a quantity of aggregate mixture, with each sieve having an open top, a substantially vertical circumferential sidewall, and a substantially planar, circular bottom, said bottom comprising a mesh and having a central aperture, with the mesh of each sieve having a plurality of apertures of substantially uniform size and with the size of the apertures of the mesh of each sieve being different than the sizes of the apertures of the mesh of each other sieve, said plurality of sieves suitably adapted to be placed within the interior of the test chamber such that the sieve with the smallest mesh apertures is placed lowest within the test chamber and the sieve with the largest mesh apertures is placed highest within the test chamber and all remaining sieves are placed within the test chamber in order of mesh aperture size with sieves having larger mesh apertures placed above sieves having smaller mesh apertures;
   a drive shaft, having an upper end and a lower end and being substantially cylindrical, said drive shaft being oriented substantially vertically and located within the interior of the test chamber, said drive shaft being suitably adapted to engage the plurality of sieves through their respective central apertures, said drive shaft being suitably adapted to rotate, simultaneously rotating each sieve engaged thereupon, said drive shaft further being suitably adapted to move in an upward vertical direction, sequentially lifting each sieve engaged thereupon; and said drive shaft further being suitably adapted to move in a downward vertical direction, sequentially lowering each sieve engaged thereupon;
   a rotary drive, located within the housing below the test chamber, suitably adapted to rotate the drive shaft;
   a lift assembly, located within the housing below the test chamber, suitably adapted to lift and lower the drive shaft;
   a weighing assembly, comprising a load cell, said weighing assembly integrated with the lift assembly and the drive shaft, suitably adapted to register the weight of the drive shaft, any sieves engaged upon the drive shaft, and any aggregate mixture contained within the sieves;
   a plurality of guide rails, corresponding in number to the maximum number of sieves, each said guide rail located within the interior of the test chamber circumferentially along the interior wall of the test chamber and proximate to the location of a sieve placed upon the drive shaft, each said guide rail being continuous and having a varying degree of slope from the horizontal, said slope changing uniformly about the circumference of said guide rail, with said slope varying, with each of the plurality of guide rails having substantially the same shape as each other guide rail, with each of the plurality of guide rails offset in relation to an adjacent guide rail by a rotation of between ten and thirty degrees, all said guide rails having the same degree of offset from adjacent guide rails, with the guide rails suitably adapted to engage with corresponding sieves such that when said sieves are rotated the varying slope of the guide rail causes the engaged sieve to tilt in a multiplicity of varying directions between positive thirty degrees to negative thirty degrees from the horizontal;
   a wash component, said wash component located within the housing and comprising
      a reservoir, suitably adapted to contain a quantity of water or other liquids,
      an inlet, said inlet integrated with the test chamber suitably adapted to introduce water or other liquids into the test chamber and onto at least one of the plurality of sieves located therein,
      an outlet, said outlet integrated with the test chamber suitably adapted to remove water or other liquids from the test chamber,
      a conduit connecting the reservoir to the inlet, and
      means for moving water or other liquids from the reservoir through the conduit and inlet;
   a heating component, said heating component located within the interior of the test chamber and suitably adapted to increase the temperature within the interior of the test chamber;
   a pressure control component, located within the housing and in connection with the test chamber, comprising a pressure lowering device and an interface between the pressure lowering device and the interior of the test chamber, said pressure control component suitably adapted to lower the pressure within the interior of the test chamber to less than ambient pressure when the access mechanism of the test chamber is in the closed state;
   a control component, said control component suitably adapted to control the operation of the rotary drive, the lift assembly, the weighing assembly, the wash component, the heating component, and the pressure control component;
a computer, having a user interface for entering and displaying data and a means for interfacing with the weighing assembly such that weights registered by the weighing assembly are received by said computer; and
computer software, suitably adapted to run on the computer and to process data received by the computer to provide a meaningful analysis of the aggregate mixture;
whereby aggregate mixtures to be analyzed are placed in the sieves and the sieves are placed into the test chamber, and an analysis is performed incorporating a combination of one or more of the steps of sieving, washing, drying, and heating the aggregate mixture while subjecting the aggregate mixture to a lower pressure, with one or more weighing operations performed on the aggregate mixture in conjunction with the foregoing steps, all such steps controlled by the control component, with results from the one or more weighing operations provided to the computer to be analyzed by the computer software.

2. The device of claim 1 wherein the test chamber further comprises one or more sensors suitably adapted to determine one or more of the following group: the opened or closed state of the access mechanism; the proper positioning of the sieves; the proper positioning of the drive shaft; the interior temperature of the test chamber; the interior atmospheric pressure of the test chamber; and the level of water or other liquids in the test chamber.

3. The device of claim 2 wherein the one or more sensors are integrated with the computer and the computer software.

4. The device of claim 1 wherein the means for interfacing the computer with the weighing assembly comprises a wired connection.

5. The device of claim 1 wherein the means for interfacing the computer with the weighing assembly comprises a wireless connection.

6. The device of claim 1 wherein the means for interfacing the computer with the weighing assembly comprises a removable storage device suitably adapted to interface with both the computer and with the weighing assembly, one at a time.

7. The device of claim 1 wherein the control component is integrated with the computer and the computer software.

8. The device of claim 1 wherein the computer interfaces with the control component by a wired connection.

9. The device of claim 1 wherein the computer interfaces with the control component by a wireless connection.

10. The device of claim 1 wherein the pressure lowering device is a vacuum pump, said vacuum pump suitably adapted to introduce a partial vacuum into the interior of the test chamber.

11. The device of claim 1 wherein the access mechanism of the test chamber comprises a hinged cover.

12. The device of claim 1 wherein
the drive shaft further comprises a pair of opposing vertical flanges, each said flange running from the upper end to the lower end of the drive shaft; and
the central aperture of each sieve comprises a pair of opposing slots, said slots suitably adapted to align with and loosely accommodate the flanges of the drive shaft; whereby a rotation of the drive shaft causes the flanges of the drive shaft to engage the slots of the central apertures of the sieves, thereby rotating the sieves simultaneously with the drive shaft, and
a lifting or a lowering of the drive shaft causes the flanges of the drive shaft to slide within the slots of the central apertures of the sieves without causing movement of the sieves.

13. The device of claim 1 further comprising
a plurality of ride rings, corresponding in number to the number of guide rails, each said ride ring associated with a guide rail, each such ride ring being substantially circular and having a plurality of engagement elements, said engagement elements suitably adapted to engage with the associated guide rail such that said ride ring rotates along the associated guide rail, with each ride ring suitably adapted to contain and engage with a sieve, such that when said sieve is rotated by the drive shaft the engaged ride ring rotates with the sieve along the guide rail, with the varying slope of the guide rail causing the ride ring and the engaged sieve to tilt in a multiplicity of varying directions as the sieve is rotated.

14. The device of claim 13 wherein the engagement elements of each ride ring are wheels suitably adapted to ride within the associated guide rail.

15. The device of claim 13 wherein
each sieve comprises a plurality of horizontal engagement flanges, each said engagement flange having an aperture; and
each ride ring comprises a plurality of upwardly disposed vertical engagement pins, each said engagement pin corresponding to an engagement flange of a corresponding sieve, with each engagement pin suitably adapted to pass through the aperture of the corresponding engagement flange from below to engage said engagement flange,
such that each said sieve and each said corresponding ride ring rotate together when the engagement flanges of said sieve are engaged with the engagement pins of said ride ring, and said engagement flanges of said sieve are suitably adapted to disengage from said engagement pins of said ride ring when said sieve is lifted by the drive shaft, thereby separating said sieve from said ride ring.

16. The device of claim 1 wherein the means for moving water or other liquids from the reservoir through the conduit and inlet is a delivery pump.

17. The device of claim 1 wherein the wash component further comprises a waste pump for moving water or other liquids from the test chamber through the outlet.

18. The device of claim 1 wherein the wash component further comprises
an outflow conduit connecting the outlet to the reservoir;
one of more filters interposed within the outflow conduit between the outlet and the reservoir; and
means for moving water or other liquids from the test chamber through the outlet and outflow conduit and into the reservoir.

19. The device of claim 18 wherein the means for moving water or other liquids from the test chamber through the outlet is a waste pump.

20. The device of claim 1 wherein the wash component further comprises
a sump tank, suitably adapted to contain a quantity of water or other liquids,
an outflow conduit connecting the outlet to the sump tank, and
means for moving water or other liquids from the test chamber through the outlet and outflow conduit and into the sump tank.

21. The device of claim 20 wherein the means for moving water or other liquids from the test chamber through the outlet is a waste pump.

22. The device of claim 1 wherein the wash component further comprises
a plurality of inlets, each said inlet integrated with the test chamber and suitably adapted to introduce water or other liquids into the test chamber and onto at least one of the plurality of sieves located therein,
a plurality of conduits corresponding in number to the number of inlets connecting the reservoir to each inlet, and
means for moving water or other liquids from the reservoir through the conduits and inlets.

23. The device of claim 22 wherein the means for moving water or other liquids from the reservoir through the conduits and inlets is a delivery pump.

24. The device of claim 22 wherein for each of the plurality of inlets the quantity of water or other liquids allowed to pass through said inlet is independently controlled.

25. The device of claim 24 wherein the wash component further comprises a valved manifold to direct water or other liquids to the plurality of inlets.

26. The device of claim 1 wherein the heating component comprises
a plurality of heating elements corresponding in number to the maximum number of sieves, each said heating element being substantially circular and located circumferentially along the interior wall of the test chamber and proximate to the location of a sieve placed upon the drive shaft, one heating element corresponding to each sieve.

27. The device of claim 26 wherein the heating elements are electric.

28. The device of claim 1 wherein the rotary drive comprises
a pulley system, said pulley system suitably adapted to engage the drive shaft and to rotate the drive shaft; and
an electric motor, suitably adapted to operate the pulley system.

29. The device of claim 28 wherein
the drive shaft further comprises a pair of opposing vertical flanges, each said flange running from the upper end to the lower end of the drive shaft; and
the pulley system of the rotary drive comprises a coupler suitably adapted to engage the drive shaft, said coupler having a pair of opposing slots, said slots suitably adapted to align with and loosely accommodate the flanges of the drive shaft;
whereby operation of the pulley system causes the coupler to rotate, with the slots of the coupler engaging the flanges of the drive shaft, thereby rotating the drive shaft simultaneously with the coupler, and
a lifting or a lowering of the drive shaft causes the flanges of the drive shaft to slide within the slots of the coupler without causing movement of the coupler.

30. The device of claim 1 wherein the lift assembly comprises
a lift plate, said lift plate being substantially planar and oriented substantially horizontally, and having an aperture suitably adapted to receive the drive shaft;
a base plate, said base plate being substantially planar and having a top surface and a perimeter, said base plate oriented substantially horizontally and below the lift plate, and having a plurality of sockets disposed on its top surface about its perimeter;
a plurality of threaded shafts, each said threaded shaft having an upper end and a lower end, each lower end of said threaded shaft suitably adapted to be placed within a socket of the base plate and suitably adapted to rotate within said socket, such that each threaded shaft is oriented substantially vertically;
a pulley system, said pulley system suitably adapted to engage the threaded shafts and to rotate the threaded shafts in two opposite rotational directions, simultaneously rotating all of the threaded shafts in the same rotational direction and at the same rotational speed; and
a reversing electric motor, suitably adapted to operate the pulley system in two opposite rotational directions; and
the load cell of the weighing assembly is substantially planar and has an upper surface and a lower surface and a perimeter, said load cell oriented substantially horizontally and interposed between the base plate and the lift plate of the lift assembly and suitably adapted to support the lower end of the drive shaft, said load cell having threaded apertures disposed on its lower surface about its perimeter, said threaded apertures substantially aligned with the upper ends of the threaded shafts of the lift assembly such that the threaded shafts pass into and through the threaded apertures of the load cell, said load cell further comprising a support structure on its upper surface, said support structure suitably adapted to support the lift plate of the lift assembly;
wherein the rotation of the threaded shafts of the lift assembly in one direction causes the load cell of the weighing assembly to move along the threads of the threaded shafts in an upward direction, lifting the lift plate of the lift assembly and the drive shaft,
such that the lift plate may come in contact with the lowermost sieve and lift said sieve, and continue to lift said sieve until said sieve comes in contact with the sieve next above and lifts that sieve, with the lift plate suitably adapted to continue upward until each sieve is contacted by and lifted by the sieve immediately below it, and
the rotation of the threaded shafts of the lift assembly in the other direction causes the load cell of the weighing assembly to move along the threads of the threaded shafts in a downward direction, lowering the lift plate and the drive shaft,
such that each sieve resting upon the sieve immediately below becomes separated from that sieve in sequence, from the uppermost sieve to the lowermost sieve, with the lift plate finally separating from the lowermost sieve.

* * * * *